US008655454B2

(12) United States Patent
Prakash et al.

(10) Patent No.: US 8,655,454 B2
(45) Date of Patent: *Feb. 18, 2014

(54) TARGETED COOLING OF DEPLOYABLE MICROWAVE ANTENNA WITH COOLING CHAMBER

(71) Applicant: Covidien LP, Mansfield, MA (US)

(72) Inventors: Mani N. Prakash, Boulder, CO (US); Tao Nguyen, Redwood City, CA (US); Christopher T. Rusin, Golden, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/945,519

(22) Filed: Jul. 18, 2013

(65) Prior Publication Data

US 2013/0304056 A1     Nov. 14, 2013

Related U.S. Application Data

(63) Continuation of application No. 13/657,609, filed on Oct. 22, 2012, now Pat. No. 8,491,580, which is a continuation of application No. 12/277,951, filed on Nov. 25, 2008, now Pat. No. 8,292,880.

(60) Provisional application No. 60/990,350, filed on Nov. 27, 2007.

(51) Int. Cl.
  *A61F 2/00* (2006.01)
  *A61B 18/04* (2006.01)
  *A61B 18/18* (2006.01)

(52) U.S. Cl.
  USPC .................. 607/101; 606/33; 606/41; 606/50

(58) Field of Classification Search
  USPC .......... 600/425, 434; 606/33, 41, 50; 607/101
  See application file for complete search history.

(56) References Cited

U.S. PATENT DOCUMENTS

| D223,367 S | 4/1972 | Kountz |
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |

(Continued)

FOREIGN PATENT DOCUMENTS

| CN | 1103807 A | 6/1995 |
| DE | 390937 C | 3/1924 |

(Continued)

OTHER PUBLICATIONS

U.S. Appl. No. 13/835,183, filed Mar. 15, 2013 Arts.

(Continued)

*Primary Examiner* — Linda Dvorak
*Assistant Examiner* — Brian M Antiskay

(57) ABSTRACT

The present disclosure relates to devices and methods for the treatment of tissue with microwave energy. The devices and methods disclosed herein utilize an antenna assembly which includes an elongate member, an outer conductor, an inner conductor, at least a portion of which is deployable, and a cooling system. The cooling system disclosed herein may significantly curtail any theoretical, or potential negative effects upon the target tissue experienced during the transmission of microwave energy to the antenna assembly due to ohmic heating.

14 Claims, 11 Drawing Sheets

(56) References Cited

U.S. PATENT DOCUMENTS

| | | |
|---|---|---|
| D295,894 S | 5/1988 | Sharkany et al. |
| 5,370,675 A | 12/1994 | Edwards et al. |
| D354,218 S | 1/1995 | Van de Peer |
| 5,458,597 A | 10/1995 | Edwards et al. |
| 5,472,441 A | 12/1995 | Edwards et al. |
| 5,486,183 A | 1/1996 | Middleman et al. |
| 5,536,240 A | 7/1996 | Edwards et al. |
| 5,549,644 A | 8/1996 | Lundquist et al. |
| 5,569,242 A | 10/1996 | Lax et al. |
| 5,688,267 A | 11/1997 | Panescu et al. |
| 5,741,225 A | 4/1998 | Lax et al. |
| 5,776,176 A | 7/1998 | Rudie |
| 5,861,021 A | 1/1999 | Thome et al. |
| 5,871,523 A | 2/1999 | Fleischman et al. |
| 5,904,690 A | 5/1999 | Middleman et al. |
| 5,921,982 A | 7/1999 | Lesh et al. |
| 6,002,968 A | 12/1999 | Edwards |
| 6,053,912 A | 4/2000 | Panescu et al. |
| D424,693 S | 5/2000 | Pruter |
| D424,694 S | 5/2000 | Tetzlaff et al. |
| D425,201 S | 5/2000 | Tetzlaff et al. |
| 6,068,629 A | 5/2000 | Haissaguerre et al. |
| 6,071,281 A | 6/2000 | Burnside et al. |
| 6,146,379 A | 11/2000 | Fleischman et al. |
| 6,165,172 A | 12/2000 | Farley et al. |
| 6,179,832 B1 | 1/2001 | Jones et al. |
| 6,280,441 B1 | 8/2001 | Ryan |
| D449,886 S | 10/2001 | Tetzlaff et al. |
| D457,958 S | 5/2002 | Dycus et al. |
| D457,959 S | 5/2002 | Tetzlaff et al. |
| 6,419,653 B2 | 7/2002 | Edwards et al. |
| 6,471,659 B2 | 10/2002 | Eggers et al. |
| 6,514,249 B1 | 2/2003 | Maguire et al. |
| 6,547,788 B1 | 4/2003 | Maguire et al. |
| 6,610,054 B1 | 8/2003 | Edwards et al. |
| 6,622,731 B2 | 9/2003 | Daniel et al. |
| 6,663,624 B2 | 12/2003 | Edwards et al. |
| 6,682,526 B1 | 1/2004 | Jones et al. |
| D487,039 S | 2/2004 | Webster et al. |
| 6,689,126 B1 | 2/2004 | Farley et al. |
| 6,786,905 B2 | 9/2004 | Swanson et al. |
| D496,997 S | 10/2004 | Dycus et al. |
| D499,181 S | 11/2004 | Dycus et al. |
| 6,852,091 B2 | 2/2005 | Edwards et al. |
| 6,869,431 B2 | 3/2005 | Maguire et al. |
| 6,893,419 B2 | 5/2005 | Noda et al. |
| 6,918,907 B2 | 7/2005 | Kelly et al. |
| 6,974,463 B2 | 12/2005 | Magers et al. |
| D525,361 S | 7/2006 | Hushka |
| 7,108,696 B2 | 9/2006 | Daniel et al. |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| 7,207,989 B2 | 4/2007 | Pike, Jr. et al. |
| D541,938 S | 5/2007 | Kerr et al |
| 7,226,446 B1 | 6/2007 | Mody et al. |
| 7,258,690 B2 | 8/2007 | Sutton et al. |
| 7,285,116 B2 | 10/2007 | de la Rama et al. |
| 7,293,562 B2 | 11/2007 | Malecki et al. |
| 7,294,127 B2 | 11/2007 | Leung et al. |
| 7,300,438 B2 | 11/2007 | Falwell et al. |
| 7,311,703 B2 | 12/2007 | Turovskiy et al. |
| 7,335,198 B2 | 2/2008 | Eggers et al. |
| D564,662 S | 3/2008 | Moses et al. |
| 7,387,626 B2 | 6/2008 | Edwards et al. |
| 7,399,299 B2 | 7/2008 | Daniel et al. |
| D576,932 S | 9/2008 | Strehler |
| 7,465,300 B2 | 12/2008 | Arless et al. |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| 7,799,019 B2 | 9/2010 | Turovskiy et al. |
| D634,010 S | 3/2011 | DeCarlo |
| 8,012,148 B2 | 9/2011 | Turovskiy et al. |
| 8,068,921 B2 | 11/2011 | Prakash et al. |
| 8,192,423 B2 | 6/2012 | Turovskiy et al. |
| 8,473,077 B2 | 6/2013 | Bonn et al. |
| 8,491,580 B2 | 7/2013 | Prakash et al. |
| 2004/0181216 A1 | 9/2004 | Kelly et al. |
| 2005/0010095 A1 | 1/2005 | Stewart et al. |
| 2005/0222558 A1 | 10/2005 | Baxter et al. |
| 2006/0015162 A1 | 1/2006 | Edward et al. |
| 2006/0106375 A1 | 5/2006 | Werneth et al. |
| 2006/0259024 A1 | 11/2006 | Turovskiy et al. |
| 2007/0043337 A1 | 2/2007 | McAuley |
| 2007/0083193 A1 | 4/2007 | Werneth et al. |
| 2007/0179496 A1 | 8/2007 | Swoyer et al. |
| 2007/0203480 A1 | 8/2007 | Mody et al. |
| 2007/0213703 A1 | 9/2007 | Naam et al. |
| 2007/0219546 A1 | 9/2007 | Mody et al. |
| 2007/0255276 A1 | 11/2007 | Sliwa et al. |
| 2007/0265610 A1 | 11/2007 | Thapliyal et al. |
| 2007/0270789 A1 | 11/2007 | Berger |
| 2007/0293854 A1 | 12/2007 | Pless et al. |
| 2007/0293855 A1 | 12/2007 | Sliwa et al. |
| 2008/0082093 A1 | 4/2008 | Prakash et al. |
| 2008/0154259 A1 | 6/2008 | Gough et al. |
| 2008/0281322 A1 | 11/2008 | Sherman et al. |
| 2010/0057074 A1 | 3/2010 | Roman et al. |
| 2010/0318078 A1 | 12/2010 | Turovskiy et al. |
| 2012/0041433 A1 | 2/2012 | Prakash et al. |
| 2012/0172860 A1 | 7/2012 | Brannan |
| 2012/0172861 A1 | 7/2012 | Brannan |
| 2012/0172862 A1 | 7/2012 | Brannan |
| 2012/0172863 A1 | 7/2012 | Brannan |
| 2012/0232544 A1 | 9/2012 | Willyard et al. |
| 2012/0232549 A1 | 9/2012 | Willyard et al. |
| 2012/0232619 A1 | 9/2012 | Turovskiy et al. |
| 2013/0030429 A1 | 1/2013 | Rusin |
| 2013/0041362 A1 | 2/2013 | Lee et al. |
| 2013/0041365 A1 | 2/2013 | Rusin et al. |
| 2013/0053695 A1 | 2/2013 | Brannan |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079765 A1 | 3/2013 | Kim et al. |
| 2013/0085488 A1 | 4/2013 | Brannan et al. |
| 2013/0103025 A1 | 4/2013 | Brannan |
| 2013/0103029 A1 | 4/2013 | Brannan |
| 2013/0126207 A1 | 5/2013 | Rossetto et al. |
| 2013/0131670 A1 | 5/2013 | Prakash |
| 2013/0178841 A1 | 7/2013 | Reid, Jr. |
| 2013/0178842 A1 | 7/2013 | Reid, Jr. |
| 2013/0178843 A1 | 7/2013 | Lee et al. |
| 2013/0178844 A1 | 7/2013 | Lee et al. |
| 2013/0190751 A1 | 7/2013 | Brannan |
| 2013/0192063 A1 | 8/2013 | Brannan |
| 2013/0218143 A1 | 8/2013 | Ross |
| 2013/0226172 A1 | 8/2013 | Peterson et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |

(56) References Cited

FOREIGN PATENT DOCUMENTS

| | | |
|---|---|---|
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 667 126 A1 | 8/1995 |
| EP | 0 836 868 A2 | 4/1998 |
| EP | 0 882 955 A1 | 12/1998 |
| EP | 0893101 A2 | 1/1999 |
| EP | 1 159 926 A2 | 12/2001 |
| EP | 1186274 | 4/2006 |
| EP | 1 905 375 A1 | 4/2008 |
| EP | 2253286 A1 | 11/2010 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 97/06739 A2 | 2/1997 |
| WO | 97/06740 A2 | 2/1997 |
| WO | 97/06855 A2 | 2/1997 |
| WO | 00/36985 A2 | 6/2000 |
| WO | 2005/112783 A1 | 12/2005 |
| WO | 2010/035831 A1 | 4/2010 |

OTHER PUBLICATIONS

U.S. Appl. No. 13/835,513, filed Mar. 15, 2013 Brannan.
U.S. Appl. No. 13/836,014, filed Mar. 15, 2013 Arts.
U.S. Appl. No. 13/836,353, filed Mar. 15, 2013 Arts.
U.S. Appl. No. 13/839,562, fFiled Mar. 15, 2013 Zheng.
U.S. Appl. No. 13/853,363, filed Mar. 29, 2013 Kim.
U.S. Appl. No. 13/867,834, filed Jul. 22, 2013 Brannan.
U.S. Appl. No. 13/871,142, filed Apr. 26, 2013 Ohri.
U.S. Appl. No. 13/886,080, filed May 2, 2013 Bahney.
U.S. Appl. No. 13/889,989, filed May 8, 2013 Lee.
U.S. Appl. No. 13/903,668, filed May 28, 2013 Podhajsky.
U.S. Appl. No. 13/904,478, filed May 29, 2013 Ohri.
U.S. Appl. 13/908,463, filed Jun. 3, 2013 Brannan.
U.S. Appl. No. 13/908,555, filed Jun. 3, 2013 Dunning.
U.S. Appl. No. 13/920,367, filed Jun. 18, 2013 Sharonov.
U.S. Appl. No. 13/920,411, filed Jun. 18, 2013 Sharonov.
U.S. Appl. No. 13/922,006, filed Jun. 19, 2013 Nau.
U.S. Appl. No. 13/942,833, filed Jul. 16, 2013 Sharonov.
U.S. Appl. No. 13/942,864, filed Jul. 16, 2013 Sharonov.
U.S. Appl. No. 13/943,452, filed Jul. 16, 2013 Behnke.
U.S. Appl. No. 13/945,519, filed Jul. 18, 2013 Prakash.
U.S. Appl. No. 13/945,718, filed Jul. 18, 2013 Rossetto.
U.S. Appl. No. 13/957,087, filed Aug. 1, 2013 Brannan.
U.S. Appl. No. 13/973,543, filed Aug. 22, 2013 Orszulak.
U.S. Appl. No. 14/011,414, filed Aug. 27, 2013 Ohri.
U.S. Appl. No. 14/011,438, filed Aug. 27, 2013 Ohri.
U.S. Appl. No. 14/014,937, filed Aug. 30, 2013 Willyard.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.

(56) References Cited

OTHER PUBLICATIONS

McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences. cndot.Yingyong Kexue Xuebao, Shangha CN, vol. 23, No. 2: (Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002, 89, 154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" Anz Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.—Medical Professionals: Targis.TM. Technology (Date Unknown). "Overcoming the Challenge" located at: <http://www.urologix.com!medicaUtechnology.html> Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993 Roger A. Stern.
U.S. Appl. No. 08/483,742, filed Jun. 7, 1995, Roger A. Stern.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

(56) References Cited

OTHER PUBLICATIONS

B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/ Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radio!, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite Element Codes to Model Electrical Heating and Non.cndot.Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

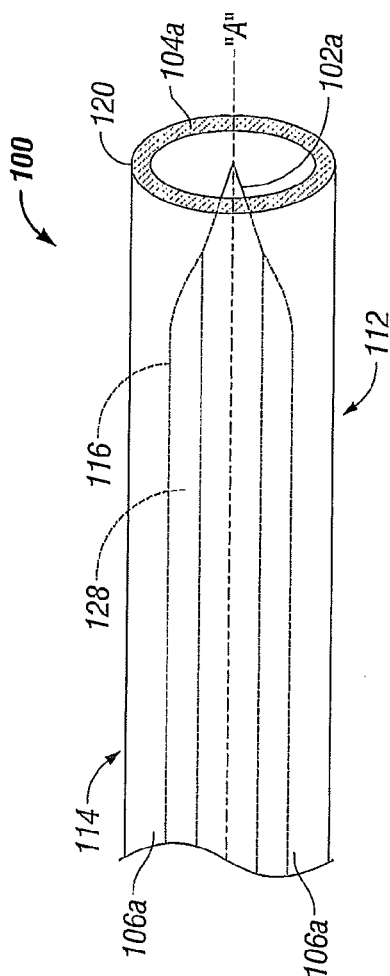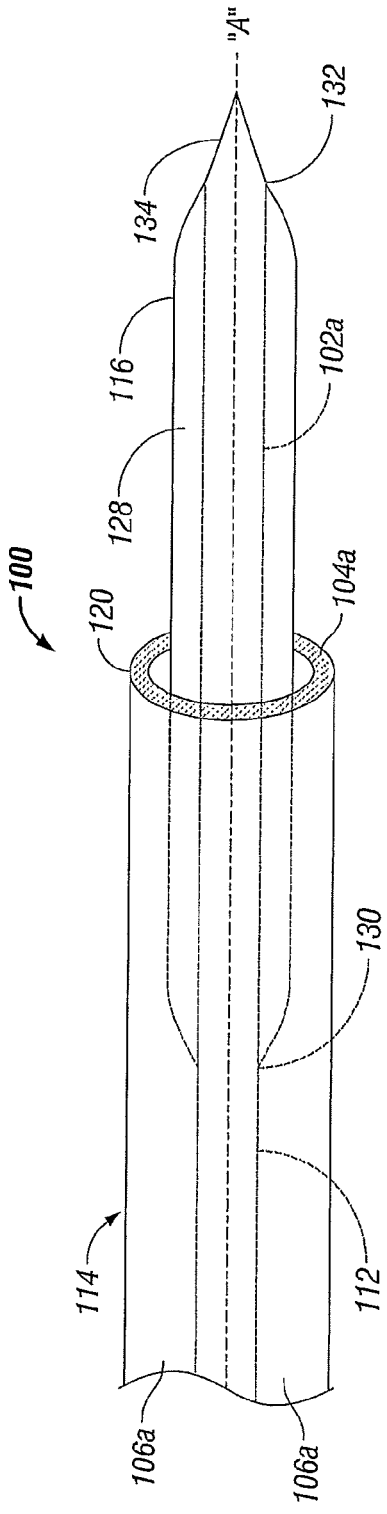

TARGETED COOLING OF DEPLOYABLE MICROWAVE ANTENNA WITH COOLING CHAMBER

CROSS-REFERENCE TO RELATED APPLICATIONS

This application is a continuation of U.S. patent application Ser. No. 13/657,609, filed Oct. 22, 2012, now U.S. Pat. No. 8,491,580, which is a continuation of U.S. patent application Ser. No. 12/277,951, filed Nov. 25, 2008, now U.S. Pat. No. 8,292,880, which claims the benefit of and priority to U.S. Provisional Patent Application Ser. No. 60/990,350, filed Nov. 27, 2007, the entire contents of all of which is hereby incorporated by reference herein.

BACKGROUND

1. Technical Field

The invention relates generally to microwave antennas that may be used in therapeutic or ablative tissue treatment applications. More particularly, the invention relates to devices and methods for regulating, maintaining, and/or controlling a temperature of microwave antennas used in such applications.

2. Background of the Related Art

Many procedures and devices employing microwave technology are well known for their applicability in the treatment, coagulation, and targeted ablation of tissue. During such procedures, the antenna of a microwave probe of the monopole, dipole, or helical variety, as is conventional in the art, is typically advanced into the patient either laparoscopically or percutaneously until the target tissue is reached.

Following the introduction of the microwave probe, during the transmission of microwave energy to the target tissue, the outer surface of the antenna may sometimes reach unnecessarily high temperatures due to ohmic heating. When exposed to such temperatures, the treatment site, as well as the surrounding tissue, may be unnecessarily and unintentionally effected. The present disclosure contemplates curtailing such tissue effects by providing improved microwave tissue treatment devices, cooling systems, and methods.

To prevent such unnecessarily high temperatures, several different cooling methodologies are conventionally employed.

SUMMARY

A need exists in the art for an improved microwave tissue treatment device incorporating a cooling or temperature control system that minimizes unnecessarily high temperatures during tissue treatment.

The present disclosure is directed to a microwave tissue treatment device for the therapeutic treatment or ablation of tissue. In one embodiment, a microwave tissue treatment device is disclosed that includes an antenna assembly having an elongate member with proximal and distal ends that defines a longitudinal axis, outer and inner conductors disposed within the elongate member that extend along the longitudinal axis, a dielectric material interposed between the outer and inner conductors, and a sleeve at least partially disposed about a distal portion of the inner conductor and defining a cavity therearound, the cavity having a proximal end and a distal end. At least a portion of the inner conductor is deployable such that the antenna assembly may transition from a first position to a second position. The device also includes a cooling system associated with the antenna assembly that includes at least one inflow member and at least one outflow member, each of which is configured to circulate at least one fluid within the cavity such that at least a section of the inner conductor is in fluid contact therewith.

The cavity defined by the sleeve may include at least two regions, such as, for example, a proximal region, an intermediate region, and a distal region. In one embodiment, the microwave tissue treatment device includes at least one baffle member for defining at least two regions of the cavity. In another embodiment, the at least one baffle member defines at least two axial dimensions within the cavity.

In yet another embodiment, the microwave tissue treatment device cooling system includes first, second, and third inflow and outflow members, the first inflow and outflow members, the second inflow and outflow members, and the third inflow and outflow members being in fluid communication with a respective proximal, intermediate, and distal regions of the cavity defined by the sleeve.

The microwave tissue treatment device may include at least one temperature sensor operatively connected to the cavity, or a region thereof.

In another embodiment, the microwave tissue treatment device includes a first baffle member and a second baffle member disposed within the cavity. The first baffle member and the proximal end of the cavity define a proximal region of the cavity of the sleeve, the first baffle member and the second baffle member define an intermediate region of the cavity, and the second baffle member and the distal end of the cavity define a distal region of the cavity. The first baffle member is configured to substantially prevent the communication of fluid between the proximal and intermediate regions, while the second baffle member is configured to substantially prevent the communication of fluid between the intermediate region and the distal region. The first baffle member and the proximal end of the cavity define a first axial dimension, while the first baffle member and the second baffle member define a second axial dimension, and the second baffle member and the distal end of the cavity define a third axial dimension. In one embodiment, the first axial dimension is greater than the second axial dimension.

In another embodiment, the proximal region of the cavity has a first internal diameter, and the intermediate and distal regions have second and third internal diameters, respectively. In one embodiment, the first internal diameter is greater than the second internal diameter, and the second internal diameter is greater than the third internal diameter.

In one embodiment of the present disclosure, at least a portion of the inner conductor has a substantially arcuate profile when deployed, whereas in an alternate embodiment, at least a portion of the inner conductor has a substantially non-arcuate profile when deployed. In another embodiment, at least a portion of the inner conductor has a substantially tapered profile.

The fluid may be chosen from the group consisting of water, saline, ammonium chloride, sodium nitrate, and potassium chloride, and the fluid may be circulated with a pump.

According to another aspect of the present disclosure, an improved microwave tissue treatment device is disclosed that includes an antenna assembly having an outer conductor and an inner conductor with a dielectric material interposed therebetween, where at least a portion of the inner conductor is deployable. The device also includes a sleeve that is at least partially disposed about a distal portion of the inner conductor, thereby defining at least one cavity, at least one baffle member disposed within the sleeve such that at least two regions of the cavity is defined, and a cooling system. The cooling system includes at least one inflow member and at least one outflow member, each of which is in fluid communication with the cavity defined by the sleeve.

According to a further aspect of the present disclosure, a method of cooling a microwave antenna includes providing a cooling system including at least one inflow and outflow member, each being in fluid communication with at least a portion of the microwave antenna, and flowing a cooling fluid through the cooling system such that the cooling fluid is in fluid communication with at least a portion of the microwave antenna.

These and other features of the microwave tissue treatment device and method of use disclosed herein will become more readily apparent to those skilled in the art from the following detailed description of various embodiments of the present disclosure.

BRIEF DESCRIPTION OF THE DRAWINGS

Various embodiments of the present disclosure are described hereinbelow with references to the drawings, wherein:

FIG. 3 is a perspective view of an antenna assembly of a microwave tissue treatment device, in accordance with an embodiment of the present disclosure, shown in a non-deployed condition;

FIG. 4 is a perspective view of the antenna assembly of FIG. 3, shown in a deployed, linear condition;

DETAILED DESCRIPTION OF THE EMBODIMENTS

Figure 1:
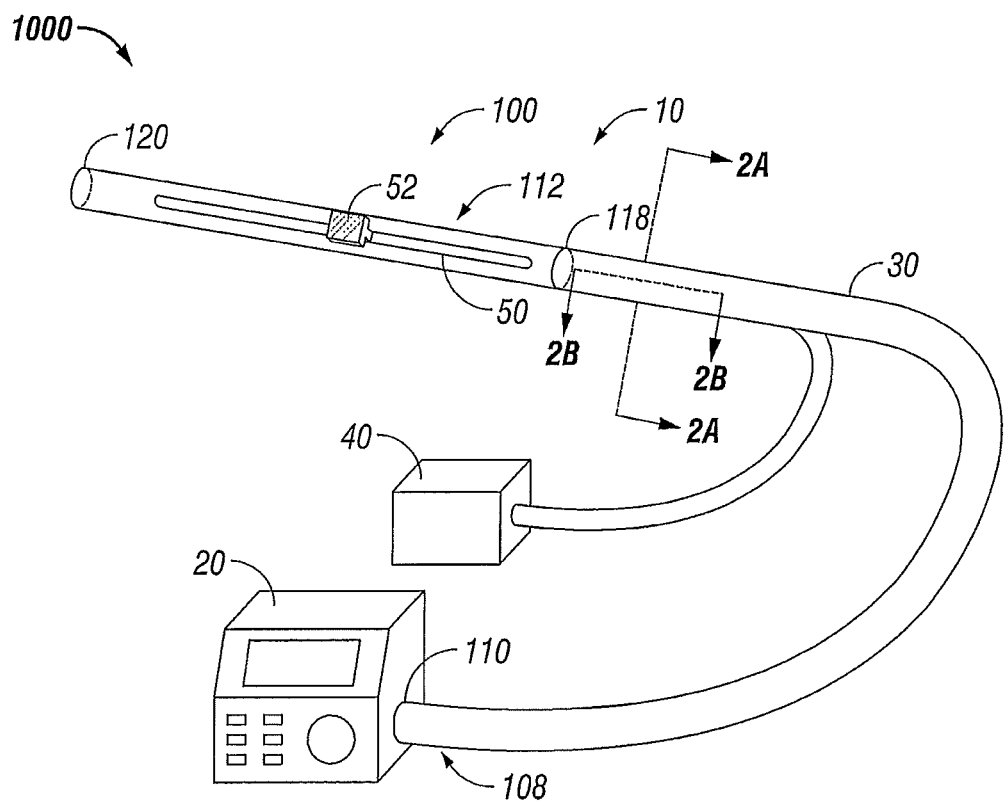
FIG. 1 is a schematic illustration of a microwave tissue treatment system including a microwave tissue treatment device, in accordance with an embodiment of the present disclosure.

In the drawings and in the description that follows, the term "proximal", as is traditional, will refer to the end of the apparatus that is closest to the clinician, while the term "distal" will refer to the end that is furthest from the clinician.

Referring now in detail to the figures, in which like references numerals identify similar or identical elements, there is illustrated, in FIG. 1, a microwave tissue treatment system 10 in accordance with the present disclosure. System 10 includes a microwave tissue treatment device 1000 having an antenna assembly 100 connected to a power source or supply 20, e.g. a microwave or RF generator or any suitable power generating device suitable for energizing the tissue treatment device 1000, through a feedline 30. Microwave tissue treatment device 1000 may include a pump 40, e.g. a peristaltic pump or the like, as a mechanism for circulating a cooling or heat dissipative fluid through device 1000, as described below. Device 1000 may further include a pusher or deployment assembly 50 that includes a deployment knob 52, where deployment knob 52 is operatively engaged with or coupled to the antenna assembly 100, as described in further detail below.

Figure 2A:
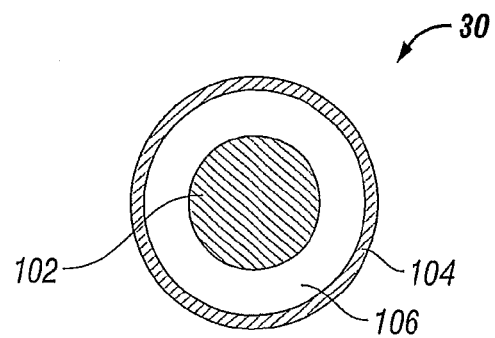
FIG. 2A is a transverse, cross-sectional view of a feedline of the microwave tissue treatment device of FIG. 1, as taken through 2A-2A of FIG. 1.
Figure 2B:
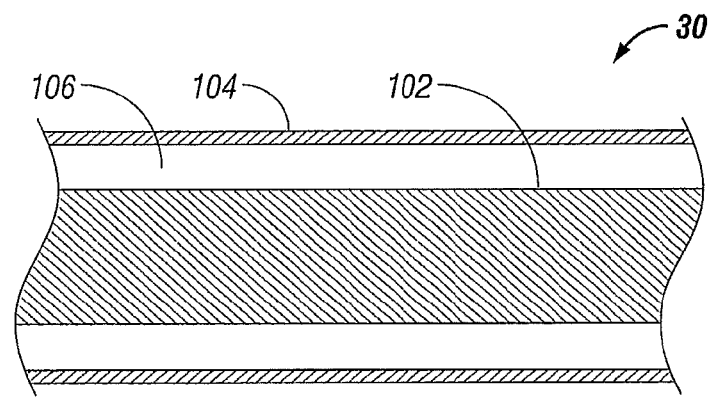
FIG. 2B is a longitudinal, cross-sectional view of the feedline of the microwave tissue treatment device of FIG. 1, as taken through 2B-2B of FIG. 1.

Referring now to FIGS. 1-2B, as indicated above, device 1000 is electrically connected to generator or power supply 20 by feedline 30. Feedline 30 may be any suitable conductive pathway capable of transferring an electrical current to tissue treatment device 1000. In one embodiment, as seen in FIGS. 2A-2B, feedline 30 may be a coaxial cable composed of an inner conductor 102, an outer conductor 104, and a dielectric 106 interposed between inner and outer conductors 102, 104 to electrically separate and/or isolate inner and outer conductors 102, 104 from one another. Inner and outer conductors 102, 104 may each be made of a suitable conductive material that may be semi-rigid or flexible, while dielectric 106 may include any number of suitable non-conductive materials such as ceramic and polytetrafluoroethylene (PTFE). Inner and outer conductors 102, 104 of feedline 30 may incorporate any suitable conductive material or metal, including, but not limited to, silver, copper and gold. In certain embodiments, inner and outer conductors 102, 104 of feedline 30 may include a conductive or non-conductive substrate plated or coated with a suitable conductive material.

Feedline 30 may range in length from about 1 foot (0.3048 m) to about 15 feet (4.572 m), or greater, if required in a particular application. As depicted in FIG. 1, feedline 30 has a proximal portion 108 operatively connected to, or connectable to, power supply 20 at proximal end 110, and a distal portion 112 that forms a part of microwave tissue treatment device 1000, as disclosed below.

Referring now to FIGS. 1, 3 and 4, microwave tissue treatment device 1000 includes an antenna assembly 100 having an elongate member 114 disposed about a distal portion 112 of feedline 30, and a sleeve 116 that at least partially surrounds a distal portion 102a of the inner conductor, as described in further detail below.

Elongate member 114 has proximal and distal ends 118, 120 and defines longitudinal axis "A". Elongate member 114 may be formed of any material suitable for electrically insulating a clinician or operator from the inner and outer conductors 102, 104 of feedline 30 disposed therein such that the antenna assembly 100 may be handled during use.

Elongate member 114 conceals a distal portion 102a (FIG. 3) of the inner conductor 102 when the microwave tissue treatment device 1000 is not in use so as to prevent unintentional damage or injury, as well as the distal portion 112 of feedline 30, which includes distal portions 102a, 104a, and 106a of the inner conductor, the outer conductor, and the dielectric, respectively. Accordingly, the inner conductor, the outer conductor, and the dielectric are not only components of the feedline 30, but also constitute components of antenna assembly 100.

At least a portion of the inner conductor, i.e. distal portion 102a, is deployable from distal portion 104a of the outer conductor, such that the antenna assembly 100 may transition from a first, non-deployed condition (FIG. 3), to a second, deployed condition during use (FIG. 4), as described in further detail below. In the first condition, the distal portion 102a of the inner conductor is at least partially disposed within the distal portion 104a of the outer conductor and the elongate member 114. In the second, deployed condition, the distal portion 102a of the inner conductor extends at least partially beyond a distal end 120 of elongate member 114, such that contact may be made with the target tissue (not shown).

Movement from the first position to the second position may be facilitated through the use of any suitable mechanism, such as, for example, a deployment assembly 50 (FIG. 1). Reference may be made to commonly owned U.S. Patent Publication No. 2004/0267156, filed Apr. 4, 2004, for a detailed discussion regarding the components and functionality of deployment assembly 50.

Figure 5:
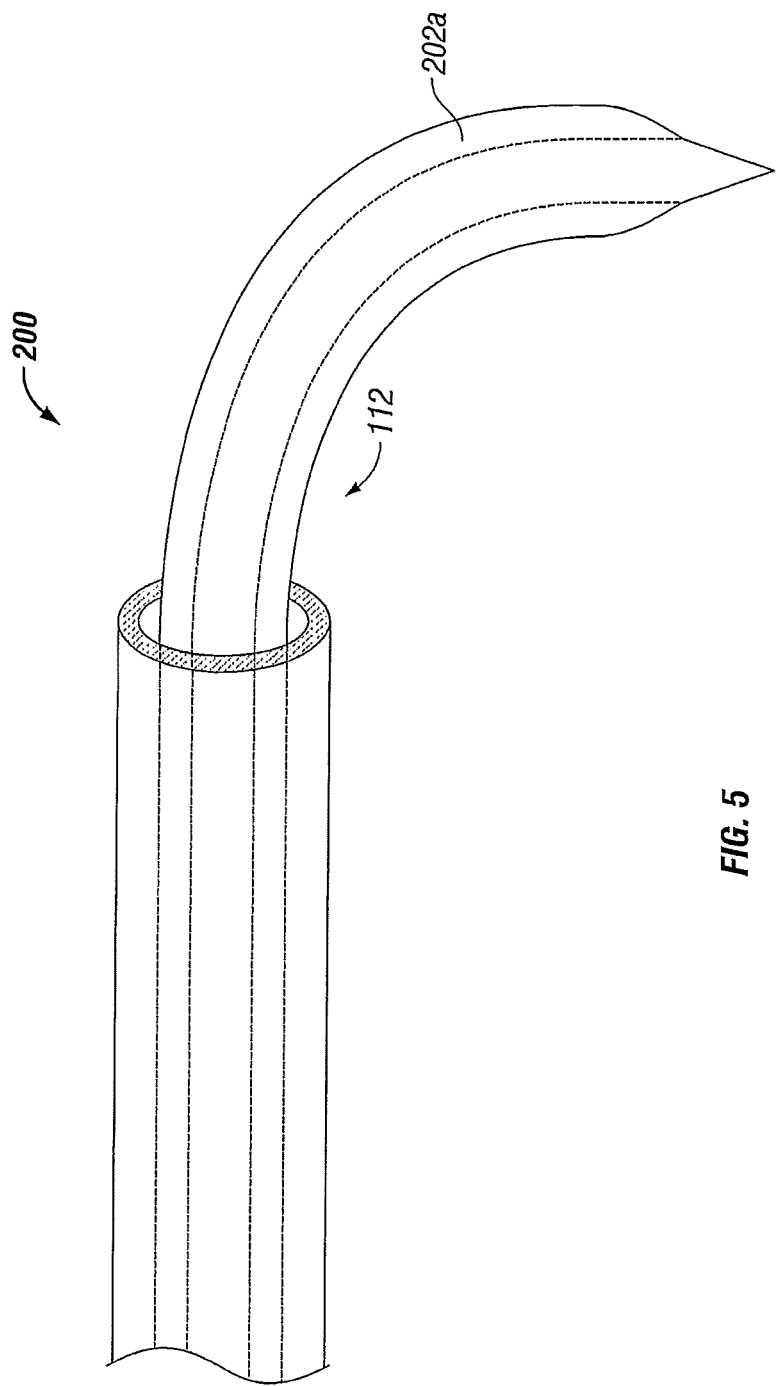
FIG. 5 is a perspective view of an antenna assembly of a microwave tissue treatment device, in accordance with an embodiment of the present disclosure, shown in a deployed, arcuate condition.

In one embodiment, as seen in FIG. 4, antenna assembly 100 includes a distal portion 102a of an inner conductor that exhibits a substantially non-arcuate profile when deployed. In an alternate embodiment, as seen in FIG. 5, antenna assembly 200 includes an inner conductor with a distal portion 202a that exhibits a substantially arcuate profile when deployed. Reference may be made to commonly owned U.S. Pat. No. 7,197,363 for a detailed discussion of the structure of arcuate microwave antenna configurations.

Figure 6:
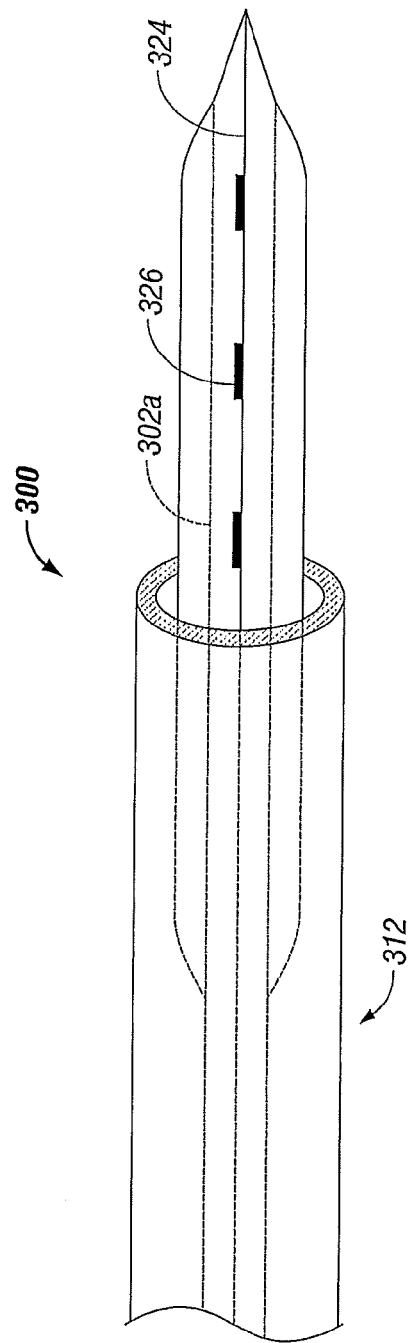
FIG. 6 is a perspective view of an antenna assembly of a microwave tissue treatment device, in accordance with another embodiment of the present disclosure, shown in a deployed condition.

In another embodiment, as seen in FIG. 6, antenna assembly 300 includes a distal portion 302a of an inner conductor that is not entirely formed of a conductive material. In this embodiment, distal portion 302a of the inner conductor includes a radiating member 324 with one or more conductive surfaces 326. Conductive surface or surfaces 326 may have a particular pattern or distribution for focusing or dispersing the energy transmitted into distal portion 302a of the inner conductor. For example, radiating member 324 may have a conductive surface 326 on only one side or in one particular area or region thereof.

Figure 7:
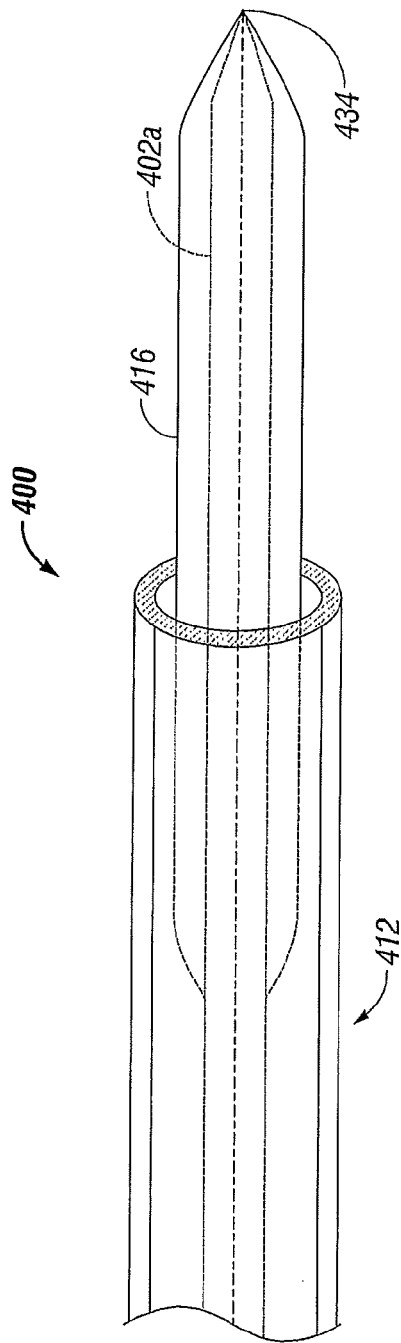
FIG. 7 is a perspective view of an antenna assembly of a microwave tissue treatment device in accordance with another embodiment of the present disclosure, shown in a deployed condition.

Referring back to FIGS. 3 and 4, sleeve 116 is disposed about distal portion 102a of the inner conductor in such a manner so as to define a cavity 128. Sleeve 116 may be fixedly, releasably, or slidably connected to distal portion 102a in any suitable manner including, but not being limited to, welding or adhering, as would be appreciated by one skilled in the art. Sleeve 116 has proximal and distal ends 130, 132 defined by the points at which sleeve 116 is connected to distal portion 102a. In one embodiment, as best seen in FIG. 4, the distal-most tip 134 of distal portion 102a extends beyond the distal end 132 of sleeve 116. In another embodiment, however, as best seen in FIG. 7, antenna assembly 400 may include a sleeve 416 connected to a distal portion 402a of an inner conductor at the distal-most tip 434 thereof, or at a point therebeyond (not shown).

Referring again to FIGS. 3 and 4, proximal end 130 of sleeve 116 may be located at any suitable location along the length of distal portion 102a of the inner conductor, dependent upon the desired volume of cavity 128. Although depicted as substantially incisive, the present disclosure contemplates that distal-most tip 134 may be substantially arcuate, duckbilled, or any other such configuration suitable for facilitating the entry of the microwave tissue treatment device into the tissue of a patient.

Sleeve 116 may be formed of any suitable biocompatible, impermeable material capable of retaining fluid therein, including and not limited to PTFE and tetrafluorethylene-perfluorpropylene (FEP). The present disclosure contemplates that sleeve 116 may be either substantially rigid, or substantially non-rigid in character.

Figure 8:
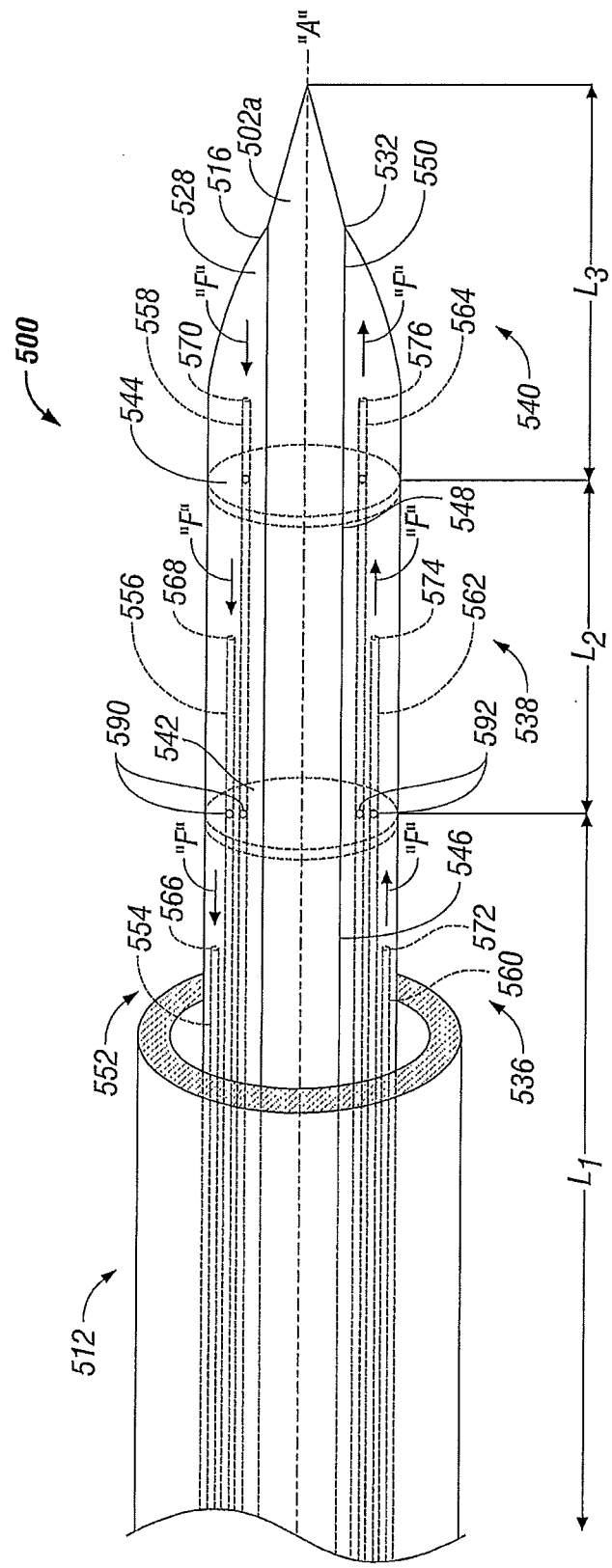
FIG. 8 is a perspective view of an antenna assembly of a microwave tissue treatment, including a cooling system, according to one embodiment of the present disclosure.
Figure 8A:
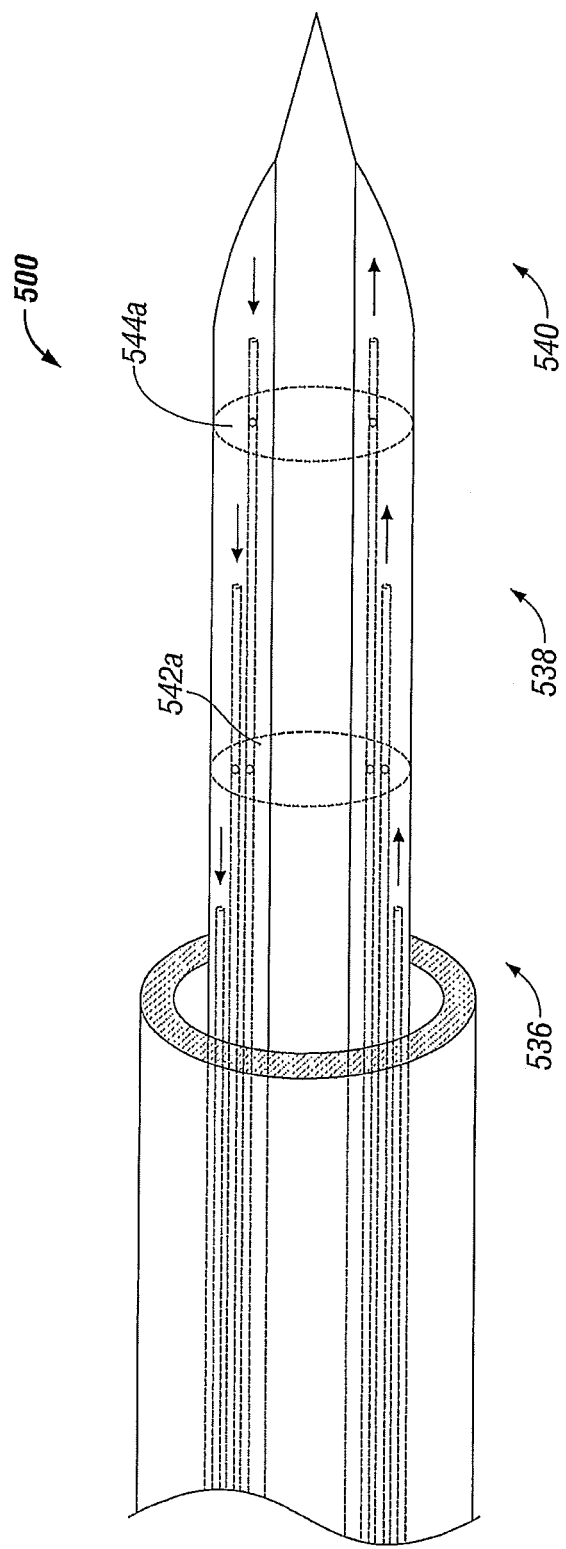
FIG. 8A is a perspective view of an antenna assembly of a microwave tissue treatment, including a cooling system, according to another embodiment of the present disclosure.

In one embodiment, as seen in FIG. 8, antenna assembly 500 includes a sleeve 516 defining a cavity 528 around a distal portion 502a of an inner conductor, and one or more baffle member(s) 542, 544 disposed within sleeve 516 that function to divide or compartmentalize cavity 528 into individual regions 536, 538, 540. Each region 536, 538, 540 defines a respective section 546, 548, 550 of the distal portion 502a of the inner conductor. In an alternate embodiment, as seen in FIG. 8A, the individual regions 536, 538, 540 are not defined by physical baffle members 542, 544 (FIG. 8), but are rather defined constructively as virtual baffle members $542_A$, $544_A$ by the interaction of a corresponding number of fluids, e.g. one fluid within each of individual regions 536, 583, 540, which may be immiscible. The incorporation of one or more fluids into antenna assembly 500 will be discussed in further detail below.

First or proximal region 536 and first section 546 of distal portion 502a have a first axial dimension $L_1$, and are defined by the location of the proximal end (not shown) of the sleeve 516 and the location of first baffle member 542. Second or intermediate region 538 and second section 548 of distal portion 502a have a second axial dimension $L_2$, and are defined by the location of first baffle member 542 and the location of second baffle member 544. And third or distal region 540 and third section 550 of distal portion 502a have a corresponding third axial dimension $L_3$, and are defined by the location of second baffle member 544 and the location of distal end 532 of sleeve 516.

In this embodiment, first and second baffle members 542, 544, respectively, serve not only to define the metes of the three regions 536, 538, 540 of cavity 528 of sleeve 516, in conjunction with the proximal end 528 (not shown) and the distal end 530 thereof, but also serve to substantially prevent any co-mingling of cooling fluid or fluids that may be circulated throughout each of the proximal, intermediate, and distal regions 536, 538, 540, as described below. The present disclosure contemplates that cavity 528 of sleeve 516 may be divided into any suitable number of regions dependent upon the requirements of the procedure and the application in which the microwave tissue treatment device may be employed.

With continued reference to FIG. 8, third or distal section 550 of the distal portion 502a of the inner conductor may comprise the area of active heating during tissue treatment or ablation. It may be desirable, therefore, to prevent the temperature in distal section 550 from reaching excessively high temperatures in order to maintain optimal energy delivery and to maintain optimal thermal therapy of the tissue. Second or intermediate section 548 of distal portion 502a may also become hot due to ohmic and conductive heating from distal section 550. Since intermediate section 548 may be in contact with the tissue surrounding the target site, it may be desirable to allow intermediate section 548 to achieve a particular temperature profile dependent upon the procedure in which the antenna assembly 500 is employed.

As an illustrative example, where coagulation of the insertion tract may be desirable, the clinician may want to allow intermediate section 548 of distal portion 502a of the inner conductor to attain a particular predetermined temperature capable of creating a coagulating effect in the insertion tract. In other applications, it may also be desirable, however, to prevent the temperature in intermediate section 548 from rising beyond a particular threshold to protect surrounding sensitive tissue structures from undesired effects. During use, first or proximal section 546 of distal portion 502a may also come into contact with the skin of a patient. Accordingly, since proximal section 546 of distal portion 502a may also be subject to ohmic and/or conductive heating, it may therefore be desirable to maintain the temperature of this section below a specific temperature, particularly in percutaneous or laparoscopic procedures, to prevent undesired effects upon the skin surface of the patient. In other procedures, such as in applications where lesions are located deep within the tissue, it may be desirable to allow the proximal section 546 to become heated to allow for the coagulation of the insertion tract.

With continued reference to FIG. 8, antenna assembly 500 further includes a cooling system 552 for regulating the temperature of distal portion 502a of the inner conductor. The cooling system 552 operates in conjunction with, and is fluidly connected to, cavity 528 of sleeve 516 such that one or more cooling or heat dissipative fluids "F" may be circulated therethrough. Fluid "F" serves to dissipate some of the heat generated by the antenna assembly 500 during use and may also act as a medium that modifies the dielectric constant of the distal portion of the antenna assembly. Potential dissipative fluids include, but are not limited to, water, saline, liquid chlorodifluoromethane, or any suitable perfluorocarbon fluid, such as Fluorinert®, distributed commercially by Minnesota Mining and Manufacturing Company (3M™), St. Paul, Minn., USA. The fluid circulated through cooling system 552 may vary depending upon the desired cooling rate and the desired tissue impedance matching properties. In various embodiments, gases, such as air, nitrous oxide, nitrogen, carbon dioxide, etc., may also be utilized as the dissipative fluid. In yet another variation, a combination of liquids and/or gases may be utilized.

During circulation, the heat dissipative fluid is in contact with those sections 546, 548, 550 of distal portion 502a of the inner conductor within respective regions 536, 538, 540 of cavity 528 defined by sleeve 516 such that the heat generated therein may be dissipated through the fluid "F". The cooling system 552 includes one or more inflow tubes 554, 556, 558, and one or more respective outflow tubes 560, 562, 564 to circulate the dissipative fluid "F". Cooling system 552 may also include at least one pump 40 (FIG. 1) in fluid communication with each inflow tube 554, 556, 558 and each outflow tube 560, 562, 564 for facilitating the circulation of the dissipative fluid "F".

Cooling system 552 may include any number of inflow and outflow tubes suitable for circulating a dissipative fluid throughout the cavity 528 defined by sleeve 516, and/or any individual regions thereof. Cooling system 552 may also employ any number of inflow and outflow members in fluid communication with each section 546, 548, 550 of distal portion 502a of the inner conductor. In some embodiments, one or more regions of cavity 528 may not be in fluid communication with cooling system 552.

As seen in FIG. 8, each of the proximal, intermediate, and distal regions 536, 538, 540, respectively, has a corresponding inflow tube 554, 556, and 558 in fluid communication therewith, and a corresponding outflow tube 560, 562, and 564 in fluid communication therewith. In particular, a proximal end (not shown) of first inflow tube 554 may be connected to pump 40 (FIG. 1), while a distal end 566 of first inflow tube 554 is in fluid communication with proximal region 536, thereby allowing dissipative fluid to flow, either constantly or intermittently, into the proximal region 536 of cavity 528 defined by sleeve 516. Upon entering proximal region 536, the dissipative fluid "F" comes into direct contact with the proximal section 546 of distal portion 502a of the inner conductor, allowing for the direct convective cooling of proximal section 546. In conjunction with first inflow tube 554, a proximal end (not shown) of first outflow tube 560 may be connected to pump 40 (FIG. 1), while a distal end 572 of first outflow tube is in fluid communication with proximal region 536, thereby allowing the dissipative fluid "F" to flow, either constantly or intermittently, out of the proximal region 536, and return to the pump 40 (FIG. 1). In so doing, during operation, heat generated by proximal section 546 of distal portion 502a of the inner conductor, disposed within the proximal region 536 of the cavity 528 defined by sleeve 516, may be regulated and/or dissipated.

As with the proximal region 536, a dissipative fluid may be pumped into and out of intermediate region 538 through respective distal ends 568, 574 of the second inflow and outflow tubes 556, 562 thereby dissipating the heat generated by the intermediate section 548 of distal portion 502a of the inner conductor through the fluid circulated therein.

Likewise, a dissipative fluid may also be circulated into and out of the distal region 540 through respective distal ends 570, 576 of the third inflow and outflow tubes 558, 564 thereby dissipating the heat generated by the distal section 550 of distal portion 502a of the inner conductor through the fluid circulated therein. In some embodiments, the fluid may act as a medium that modifies the dielectric constant of the antenna.

With continuing reference to FIG. 8, inflow tubes 554, 556, 558 may enter cavity 528 through apertures (not shown) at the proximal end of sleeve 516 (not shown). First inflow tube 554 and first outflow tube 560 are configured such that their respective distal ends 568, 580 are in fluid communication with proximal region 536. Second and third inflow tubes 556, 558 and second and third outflow tubes 562, 564 may continue through proximal region 536, through apertures 590 in first baffle member 542, and into intermediate region 538. Second inflow tube 556 and second outflow tube 562 are configured such that their respective distal ends 572, 584 are in fluid communication with intermediate region 538. Third inflow and outflow tubes 558, 564 continue through intermediate region 538, through apertures 590 in second baffle member 544, and into distal region 540. Third inflow and outflow tubes 558, 564 are configured such that their respective distal ends 576, 588 are in fluid communication with distal region 540.

In this embodiment, each of the proximal end of the cavity 528, the first baffle member 542, and the second baffle member 544 include seal members 592 associated with apertures 590. Seal members 592 may be any member suitable to substantially prevent the escape of any fluid contained within respective regions of cavity 528, through the apertures 590, including, and not limited to a seal, gasket, or the like. Seal members 592 may be formed of any suitable material, including and not limited to, a polymeric material. Seal members 592 may also substantially prevent the intermingling of the cooling fluids circulated through each of the proximal, intermediate, and distal regions 536, 538, 540 of cavity 528.

Figure 8B:
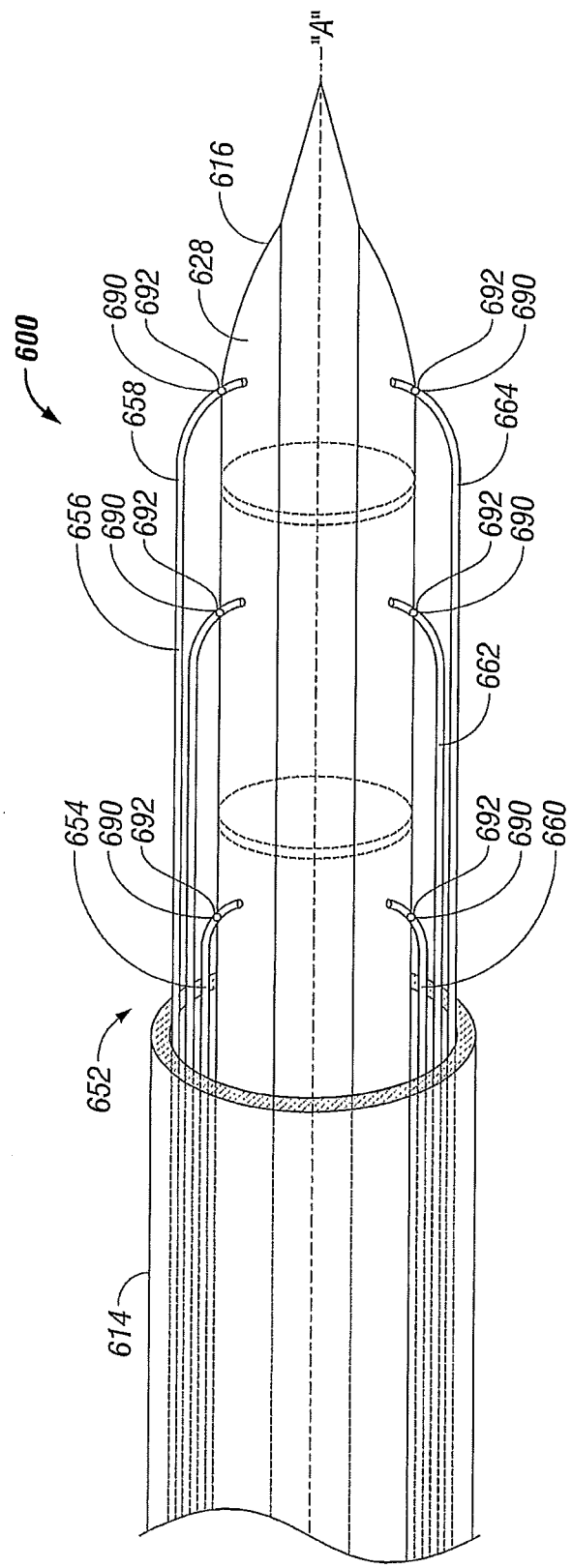
FIG. 8B is a perspective view of an antenna assembly of a microwave tissue treatment device, including a cooling system, according to still another embodiment of the present disclosure.

Referring momentarily to FIG. 8B, antenna assembly 600 includes a cooling system 652 having inflow tubes 654, 656, 658 and outflow tubes 660, 662, 664. In this embodiment, inflow tubes 654, 656, 658 and outflow tubes 660, 662, 664 enter cavity 628 defined by sleeve 616 through apertures 690 formed therein. In this embodiment, inflow tubes 654, 656, 658 may traverse elongate member 614 along its outer surface, connecting to either a common pump 40 (FIG. 1), or to individual pumps, as described above. Correspondingly, outflow tubes 660, 662, 664 may also traverse the outer surface of elongate member 116, connecting to either the common pump 40 (FIG. 1) or to the individual pumps. In this embodiment, sleeve 616 is adapted with sealing member or members 692 at apertures 690 to substantially prevent the escape of any fluid contained in cavity 628 defined by sleeve 616 through apertures 690.

Figure 8C:
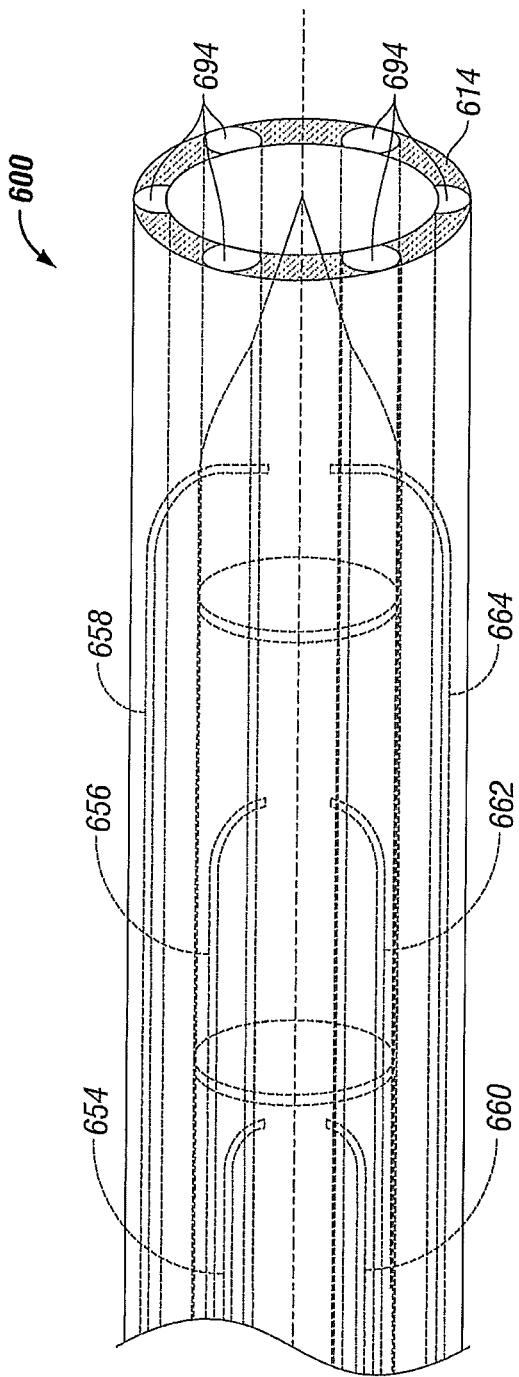
FIG. 8C is a perspective view of an antenna assembly of a microwave tissue treatment device, including a cooling system, according to yet another embodiment of the present disclosure.
Figure 8D:
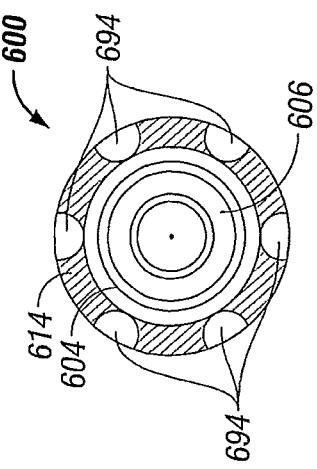
FIG. 8D is a front view of the antenna assembly of FIG. 8C.

In another embodiment, as seen in FIGS. 8C-8D, antenna assembly 600 may include one or more channels 694 formed in the elongate member 614 that are configured to respectively receive at least a portion of inflow tubes 654, 656, 658 and outflow tubes 660, 662, 664. Alternatively, channels 694 may be formed in outer conductor 604, dielectric material 606, or in any other suitable location.

Referring again to FIG. 8, given the desirability of controlled heating and temperature regulation within the individual sections 546, 548, and 550 of distal portion 502a of the inner conductor and the corresponding regions 536, 538, and 540 of the cavity 528, the axial locations of first and second baffle members 542, 544 within cavity 528 may be varied as desired or necessary. By varying the location of baffle members 542 and 544 in different embodiments, the axial length of the proximal, intermediate and distal regions 536, 538, and 540 may be varied. In varying the axial length of a region, the overall volume of that region may be varied, and accordingly, the volume of dissipative fluid circulated within that region may also be varied. As would be appreciated by one of ordinary skill in the art, an inverse relationship exists between the volume of dissipative fluid within a particular region of the cavity 528 and the temperature of that region, in that as the volume of fluid is increased, the temperature of the region will decrease. As an additional means of regulating temperature, the flow rate of fluid "F" into each regions 536, 538, and 540 of the cavity 528 may be controlled or varied, e.g. through the use of multiple pumps (not shown).

The baffle members 542, 544 may be located at any suitable or desired point within the cavity 528 defined by the sleeve 516. In one embodiment, baffle members 542, 544 are positioned such that the first, second and third axial dimensions, $L_1$, $L_2$, and $L_3$, respectively, of proximal, intermediate, and distal regions 536, 538, 540 are substantially equivalent. In another embodiment, baffle members 542, 544 are positioned such that the first axial dimension $L_1$, of proximal region 536, is greater than the second and third axial dimensions $L_2$ and $L_3$, respectively, of intermediate and distal regions 538, 540. In yet another embodiment, baffle members 542, 544 are positioned such that the third axial dimension $L_3$, of distal region 540, is greater than the first and second axial dimensions $L_1$ and $L_2$, respectively, of proximal and intermediate regions 536, 538. In alternate embodiments, the present disclosure contemplates locating the baffle members 542, 544 such that the overall volume of the cavity 528 may be distributed amongst any individual regions thereof in any suitable manner.

Figure 9:
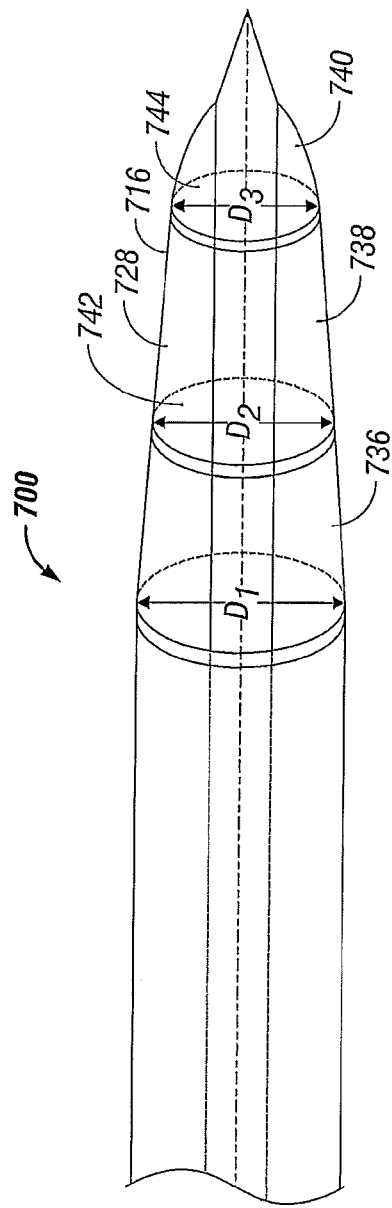
FIG. 9 is a side, plan view of an antenna assembly of a microwave tissue treatment device in accordance with another embodiment of the present disclosure.
Figure 12:
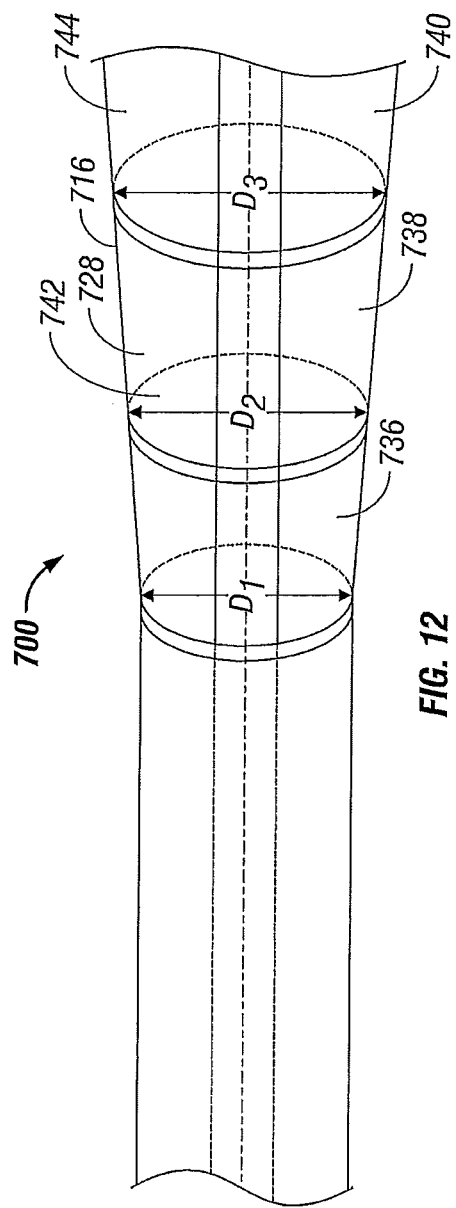
FIG. 12 is a side, plan view of an antenna assembly of a microwave tissue treatment device in accordance with another embodiment of the present disclosure.

Referring now to FIGS. 9 and 12, in other embodiments, antenna assembly 700 includes a sleeve 716 that defines a cavity 728 having proximal, intermediate, and distal regions 736, 738, and 740 defined by first and second baffle members 742, 744. In this embodiment, proximal, intermediate, and distal regions 736, 738, and 740 have a first, a second, and a third radial dimension or diameter $D_1$, $D_2$, and $D_3$, respectively. In accordance with the present disclosure, radial dimensions $D_1$, $D_2$, and $D_3$ of the proximal, intermediate, and distal regions 736, 738, and 740 may be varied so as to control the volume of each region, and accordingly, the volume of dissipative fluid circulated therethrough. By varying the volume of dissipative fluid circulated through each individual region 736, 738, and 740 of the cavity 728, the temperature of each region may be substantially regulated, as discussed above.

In one embodiment, the first, second and third radial dimensions, $D_1$, $D_2$, and $D_3$, respectively, are substantially equivalent. In another embodiment, as illustrated in FIG. 9, the first radial dimension $D_1$, of proximal region 736, is greater than the radial dimensions $D_2$ and $D_3$, respectively, of intermediate and distal regions 738 and 740. In yet another embodiment, as illustrated in FIG. 12, the third radial dimension $D_3$, of distal region 740, is greater than the radial dimensions $D_1$ and $D_2$, respectively, of proximal and intermediate regions 736 and 738. In alternate embodiments, the present disclosure contemplates that the radial dimensions $D_1$, $D_2$, and $D_3$, respectively, of each region 736, 738, and 740 of the cavity 728 defined by the sleeve 716, may be varied in any suitable manner.

Figure 10:
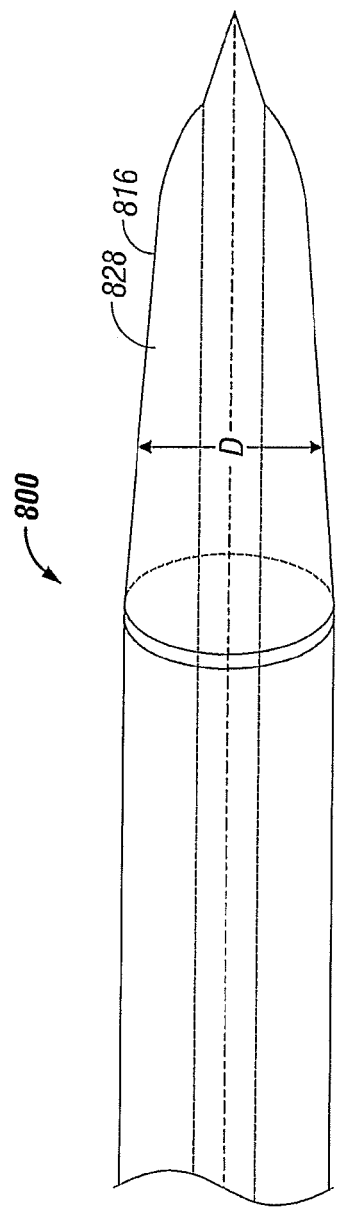
FIG. 10 is a side, plan view of an antenna assembly of a microwave tissue treatment device in accordance with yet another embodiment of the present disclosure.

Referring now to FIG. 10, in one embodiment, the present disclosure contemplates an antenna assembly 800 that includes a sleeve 816 defining a cavity 828 with a radial dimension D. In this embodiment, radial dimension D of cavity 828 is varied in a continuously decreasing manner over the axial length thereof, such that a generally tapered profile is exhibited. While the antenna assembly 800 includes a sleeve 816 defining a cavity 828 that is not compartmentalized into any regions, the tapered profile may be applicable to any of the embodiments disclosed herein above.

Figure 11:
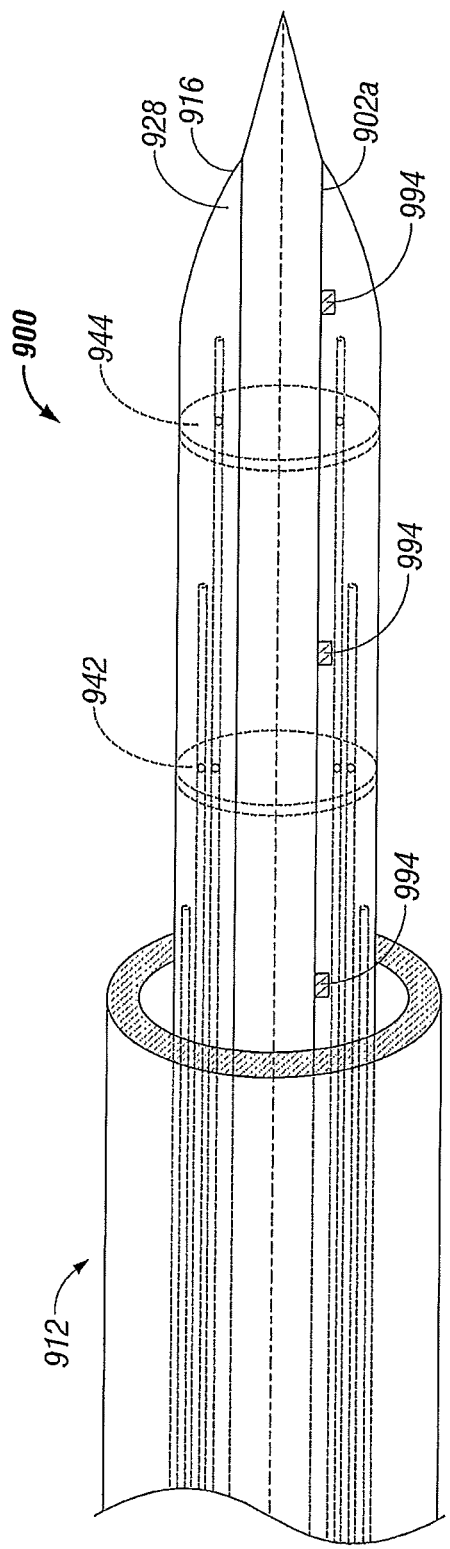
FIG. 11 is a perspective view of an antenna assembly of a microwave tissue treatment device in accordance with another embodiment of the present disclosure, shown in a deployed condition.

In another embodiment, seen in FIG. 11, an antenna assembly 900 is disclosed that includes one or more temperature sensors 994 coupled to a distal portion 902a of an inner conductor for monitoring a temperature fluctuation at or about the distal portion 902a. It may be desirable to monitor the temperature of the distal portion 902a, and/or the tissue that may come into contact therewith, or with sleeve 916, in an effort to guard against overheating and/or the unintended therapeutic effects on the tissue. This may be particularly useful in applications where microwave energy is used for treating or ablating tissue around the radiating portion. In alternate embodiments, temperature sensors 994 may be coupled or otherwise incorporated into antenna assembly 900 at any suitable location, including, but not being limited to sleeve 916, such that the temperature of the distal portion 902a of the inner conductor and/or the cavity 928 may be monitored. In various embodiments, temperature sensor or sensors 994 may be located on the sleeve 916, e.g., on an external surface thereof, or within the sleeve 916, e.g., within the cavity 928 which the sleeve 916 defines, using any suitable means, e.g. adhesives. The temperature sensor or sensors 994 may be located on a baffle member or members 942, 944, if any. Temperature sensors 994 may be configured for electrical connection to power source 20 (FIG. 1).

The temperature sensor or sensors 994 may be a semiconductor-based sensor, a thermister, a thermocouple or other temperature sensor that would be considered as suitable by one skilled in the art. An independent temperature monitor (not shown) may be coupled to the temperature sensor. Alternatively, a power supply with an integrated temperature monitoring circuit (not shown), such as one described in U.S. Pat. No. 5,954,719, may be used to modulate microwave power output supplied to the antenna assembly. Other physiological signals, e.g. EKG, may also be monitored by other medical instrumentation well known to one skilled in the art and such data applied to control the microwave energy delivered to the antenna assembly.

A closed loop control mechanism, such as a feedback controller with a microprocessor, may be implemented for controlling the delivery of energy, e.g., microwave energy, to the target tissue based on temperature measured by the temperature sensor or sensors 994.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A microwave ablation probe, comprising:
    a tubular elongated member defining a longitudinal axis and having proximal and distal ends and inner and outer surfaces, the tubular elongated member further including a plurality channels defined in the inner surface thereof;
    an outer conductor disposed along the longitudinal axis within the tubular elongated member;
    a dielectric material disposed coaxially within the outer conductor;
    an antenna disposed coaxially within the dielectric material, the antenna extending distally from a distal end of the outer conductor, the antenna comprising:
        an inner conductor disposed coaxially within the dielectric material; and
        a cooling sleeve disposed coaxially about a distal portion of the inner conductor having a cooling chamber defined therein;
    at least one inflow conduit in fluid communication with the cooling chamber and configured to deliver coolant thereto; and
    at least one outflow conduit in fluid communication with the cooling chamber and configured to remove coolant therefrom.

2. The microwave ablation probe according to claim 1, wherein the plurality of channels are defined along the longitudinal axis of the tubular elongated member.

3. The microwave ablation probe according to claim 1, wherein at least one of the plurality of channels is configured to receive the at least one inflow conduit.

4. The microwave ablation probe according to claim 1, wherein at least one of the plurality of channels is configured to receive the at least one outflow conduit.

5. The microwave ablation probe according to claim 1, wherein the cooling chamber includes a baffle radially separating the cooling chamber into a first cooling region and a second cooling region.

6. The microwave ablation probe in accordance with claim 5, wherein the at least one inflow conduit includes a first inflow conduit in fluid communication with the first cooling region and a second inflow conduit in fluid communication with the second cooling region; and the at least one outflow conduit includes a first outflow conduit in fluid communication with the first cooling region and a second outflow conduit in fluid communication with the second cooling region.

7. The microwave ablation probe in accordance with claim 1, further including at least one temperature sensor configured to sense a temperature of the antenna.

8. The microwave ablation probe in accordance with claim 1, wherein the cooling sleeve is formed from a substantially rigid material.

9. The microwave ablation probe in accordance with claim 1, wherein the cooling sleeve is formed from a substantially non-rigid material.

10. A microwave ablation probe, comprising:
    a tubular elongated member defining a longitudinal axis and having proximal and distal ends and inner and outer surfaces, the tubular elongated member including a plurality of channels defined in the inner surface thereof;
    an outer conductor disposed along the longitudinal axis within the tubular elongated member;
    a dielectric material disposed coaxially within the outer conductor;
    an inner conductor disposed coaxially within the dielectric material;
    an antenna disposed coaxially within the elongated member and wherein the antenna member extends distally from the elongated member, the antenna assembly including a cooling sleeve having a plurality of cooling chambers disposed coaxially about the inner conductor;
    a plurality of inflow conduits disposed within at least one of the plurality of channels, each one of the plurality of inflow conduits in fluid communication with a corresponding one of the plurality of cooling chambers;
    a plurality of outflow conduits disposed within at least one of the plurality of channels, each one of the plurality of outflow conduits in fluid communication with a corresponding one of the plurality of cooling chambers; and
    a plurality of temperature sensors, each one of the plurality of temperature sensors associated with a corresponding one of the plurality of cooling chambers and configured to sense a temperature thereof.

11. The microwave ablation probe in accordance with claim 10, wherein the plurality of cooling chambers are separated by at least one baffle radially positioned therebetween.

12. The microwave ablation probe in accordance with claim 11, wherein the baffle is configured to substantially prevent fluid communication between the plurality of cooling chambers.

13. The microwave ablation probe in accordance with claim 10, wherein a first of the plurality of cooling chambers includes a first longitudinal dimension and a second of the plurality of cooling chambers includes a second longitudinal dimension that is different from the first longitudinal dimension.

14. The microwave ablation probe in accordance with claim 10, wherein a first of the plurality of cooling chambers includes a first radial dimension and a second of the plurality of cooling chambers includes a second radial dimension that is different from the first radial dimension.

* * * * *